United States Patent
Hardacre et al.

(10) Patent No.: US 7,119,235 B2
(45) Date of Patent: Oct. 10, 2006

(54) PROCESS UTILIZING ZEOLITES AS CATALYSTS/CATALYST PRECURSORS

(75) Inventors: Christopher Hardacre, Belfast (GB); David W. Rooney, Kinallen (GB); Jillian M. Thompson, Kinallen (GB); Suhas P. Katdare, Belfast (GB)

(73) Assignee: The Queen's University of Belfast, Belfast (GB)

( * ) Notice: Subject to any disclaimer, the term of this patent is extended or adjusted under 35 U.S.C. 154(b) by 0 days.

(21) Appl. No.: 10/491,451

(22) PCT Filed: Oct. 2, 2002

(86) PCT No.: PCT/GB02/04439

§ 371 (c)(1),
(2), (4) Date: Oct. 29, 2004

(87) PCT Pub. No.: WO03/028882

PCT Pub. Date: Apr. 10, 2003

(65) Prior Publication Data

US 2005/0049438 A1    Mar. 3, 2005

(30) Foreign Application Priority Data

Oct. 2, 2001  (GB) ................. 0123595.1

(51) Int. Cl.
*C07C 45/00* (2006.01)
(52) U.S. Cl. .................... 568/322; 568/323; 568/332; 568/335
(58) Field of Classification Search ............... 568/322, 568/323, 332, 335
See application file for complete search history.

(56) References Cited

U.S. PATENT DOCUMENTS

| | | |
|---|---|---|
| 5,397,454 A | 3/1995 | Zones et al. |
| 5,817,878 A | 10/1998 | Spagnol et al. |
| 6,288,281 B1 | 9/2001 | Nemeth et al. |

FOREIGN PATENT DOCUMENTS

| | | |
|---|---|---|
| WO | WO 99/03163 | 1/1999 |
| WO | WO 99/19288 | 4/1999 |
| WO | WO 00/32572 | 6/2000 |
| WO | WO 01/32308 | 5/2001 |
| WO | WO 02/072260 A2 | 9/2002 |

*Primary Examiner*—Sikarl A. Witherspoon
(74) *Attorney, Agent, or Firm*—Hodgson Russ LLP (57) ABSTRACT

According to one aspect of the invention, there is provided the use of an organic ionic liquid in a zeolite-catalysed process, for example an acylation, alkylation, isomerisation or hydrocracking process in which zeolites act as catalysts or catalyst precursors, especially Friedel-Crafts alkylation and acylation procedures.

35 Claims, 3 Drawing Sheets

PROCESS UTILIZING ZEOLITES AS CATALYSTS/CATALYST PRECURSORS

This application is a 371 of PCT/GB02/04439, filed Oct. 2, 2002, and published as WO 03/028882 on Apr. 10, 2003.

This invention relates to processes utilising zeolites as catalysts and/or catalyst precursors.

Heterogeneous catalysts are widely used in the bulk and fine chemical industry and processes catalysed by zeolites are of particular importance. A range of reactions can be catalysed using zeolites, including, for example alkylations, hydrocracking and isomerisation reactions.

In many such processes, it is highly desirable to obtain increases of yield, conversion and reaction rates. Additionally, especially in processes that are carried out with one or more of the reactants and/or products in solution, it is important that the separation of desired products and recovery of catalyst is facilitated.

The present invention is based upon the unexpected finding that ionic liquids are especially advantageous for use as components of reaction media used for carrying out processes in which zeolites act as catalysts or catalyst precursors.

SUMMARY OF INVENTION

According to one aspect of the invention, there is provided the use of an organic ionic liquid in a zeolite-catalysed process, for example an acylation, alkylation, isomerisation or hydrocracking process in which zeolites act as catalysts or catalyst precursors, especially Friedel-Crafts alkylation and acylation procedures. The invention may also be defined as providing the use of an organic ionic liquid, as or as a component of, a reaction medium for a reaction catalysed by a zeolite.

The use according to the invention is especially applicable to electrophilic substitution processes, particularly Friedel-Crafts acylation reactions, including acylation with aliphatic acylating agents containing 1–10, preferably 1–6 carbon atoms and acylations utilising aromatic acylating agents containing from 6 to 20 carbon atoms, e.g. benzoylation processes.

Acylating agents useful in the process of the invention may be selected from linear or branched aliphatic carboxylic acid halides, linear or branched aliphatic carboxylic acid anhydrides, saturated or unsaturated cycloaliphatic carboxylic acid halides, and saturated or unsaturated cycloaliphatic carboxylic acid anhydrides and ketenes.

Acylating agents used in accordance with the invention include compounds of the general formulae and wherein each $R^1$ and $R^2$, which may be the same or different, represents a substituted or unsubstituted aliphatic, aromatic or heterocyclic group containing from 1 to 40, preferably 1 to 25 and most preferably 1 to 10 carbon atoms, and X represents a leaving group.

Thus, for example, each of $R^1$ and $R^2$ may be the same or different and each is independently selected from:

$C_1$ to $C_{40}$ straight chain or branched alkyl which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;

$C_3$ to $C_8$ cycloalkyl wherein said alkyl or cycloalkyl group may be substituted with 1–3 substituents independently selected from: $C_6$ to $C_{10}$ aryl, $C_8$–$C_{20}$ aralkyl, $C_8$–$C_{20}$ alkaryl, $C_3$ to $C_8$ cycloalkyl, hydroxyl, F, $CF_3$, =O, $COOR^3$, or $OR^3$ wherein $R^3$ is selected from H, $C_1$ to $C_{20}$ alkyl and $C_6$ to $C_{10}$ aryl; or $C_6$ to $C_{10}$ aryl wherein said aryl group may be substituted with 1–3 substituents independently selected from $C_1$ to $C_{10}$ alkyl, hydroxyl, F, $CF_3$, $COOR^4$, or $OR^4$ wherein $R^4$ is selected from H, $C_1$ to $C_{20}$ alkyl; and $C_6$ to $C_{10}$ aryl, which may be substituted with 1–3 substituents independently selected from: $C_6$ to $C_{10}$ aryl, $C_8$–$C_{20}$ aralkyl, $C_8$–$C_{20}$ alkaryl, $C_3$ to $C_8$ cycloalkyl, hydroxyl, F, $CF_3$, =O, or $OR^3$ wherein $R^3$ is selected from H, $C_1$ to $C_{20}$ alkyl and $C_6$ to $C_{10}$ aryl.

Specific examples of acylating agents include: acetic anhydride, propanoic anhydride, isobutyric anhydride, trifluoroacetic anhydride, monochloroacetyl anhydride, dichloroacetyl anhydride, acetyl chloride, monochloroacetyl chloride, dichloroacetyl chloride, propanoyl chloride, isobutanoyl chloride, pivaloyl chloride, and crotonyl chloride.

There are no particular constraints on the structure of the reaction partners that may be subjected to acylation in accordance with the invention, other than that any labile substituents that might undergo unwanted side-reactions should be suitably protected. E.g. hydroxyl groups and amino groups could be protected by etherification and amidation respectively (see, e.g. Greene, T. W., Protective Groups in Organic Synthesis: Wiley: New York, 1981). Generally, reaction partners that may be subjected to acylation in accordance with the invention will have at least one mono or polycyclic aromatic nucleus, which may optionally include from 1 to 4 hetero atoms selected from N, S and O. The aromatic nucleus may contain from 6 to 20, more preferably from 6 to 10 carbon atoms. The invention also includes intramolecular acylation reactions in which an electrophilic moiety (e.g. a substituent on an aromatic ring) undergoes an intramolecular electrophilic addition to form a bicyclic structure. For example, in this regard, a compound of Formula (I) above could undergo intramolecular acylation.

Thus the acylating agent may also comprise a linear aliphatic acid halide substituent, a carboxylic acid substituent, or an acid anhydride substituent, said substituent being attached to a ring carbon atom of the aromatic substrate such that the reaction results in an intramolecular acylation reaction to form a fused ring, e.g.:

In summary, preferred are acylating agents comprising a $C_4$ to $C_{10}$ cyclic aliphatic acid halide, a $C_2$ to $C_{20}$ linear or branched aliphatic acid halide or a $C_7$ to $C_{20}$ aromatic acid halide; a $C_2$ to $C_{20}$ carboxylic acid; and a $C_4$ to $C_{20}$ acid anhydride; or the acylating agent is a $C_3$ to $C_5$ linear aliphatic acid halide substituent or a $C_3$ to $C_5$ carboxylic acid substituent said substituent being attached to a ring carbon atom of the aromatic substrate such that the reaction is an intramolecular acylation reaction to form a fused ring.

Especially preferred are acylating agents comprising a $C_2$ to $C_{20}$ linear or branched aliphatic acid halide; or a $C_3$ to $C_5$ linear aliphatic acid halide substituent said substituent being attached to a ring carbon atom of the aromatic substrate such that the reaction is an intramolecular acylation to form a fused ring.

Particularly preferred acylating agents include acid halides or the acylating agent can be an acid halide substituent present on the aromatic substrate. Acid chlorides or acid chloride substituents are especially preferred.

Exemplary structures of suitable reaction partners include the following, although other reaction partners of different structure may, of course be employed:

wherein each of $R^1$, $R^2$, $R^3$, $R^4$, $R^5$ and $R^2$, which may be the same or different and each is independently selected from:
- hydrogen, halogen (F, Cl, Br), nitro, trifluoromethyl, —$COOR^a$, OH, $OR^a$
- $C_1$ to $C_{40}$ straight chain or branched alkyl which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;
- $C_3$ to $C_8$ cycloalkyl wherein said alkyl or cycloalkyl group may be substituted with 1–3 substituents independently selected from: $C_6$ to $C_{10}$ aryl, $C_8$–$C_{20}$ aralkyl, $C_8$–$C_{20}$ alkaryl, $C_3$ to $C_8$ cycloalkyl, hydroxyl, $CF_3$, =O, $COOR^3$, or $OR^3$ wherein $R^3$ is selected from H, $C_1$ to $C_{20}$ alkyl and $C_6$ to $C_{10}$ aryl; or $C_6$ to $C_{10}$ aryl wherein said aryl group may be substituted with 1–3 substituents independently selected from $C_1$ to $C_{10}$ alkyl, hydroxyl, F, $CF_3$, $COOR^4$, or $OR^4$ wherein $R^4$ is selected from H, $C_1$ to $C_{20}$ alkyl; and
- $C_6$ to $C_{10}$ aryl, which may be substituted with 1–3 substituents independently selected from: $C_6$ to $C_{10}$ aryl, $C_8$–$C_{20}$ aralkyl, $C_8$–$C_{20}$ alkaryl, $C_3$ to $C_8$ cycloalkyl, hydroxyl, F, $CF_3$, =O, or $OR^3$ wherein $R^3$ is selected from H, $C_1$ to $C_{20}$ alkyl and $C_6$ to $C_{10}$ aryl;

each Z represents CH, N, O, S, SO or $SO_2$,
rings "X" represent fused cycloalkyl, heterocycloalkyl, aryl or heteroaryl groups; and
$R^a$ represents $C_1$ to $C_6$ straight chain or branched alkyl which may be substituted by one to three groups selected from: $C_1$ to $C_6$ alkoxy, $C_6$ to $C_{10}$ aryl, CN, OH, $NO_2$, $C_1$ to $C_6$ aralkyl and $C_1$ to $C_6$ alkaryl;
$C_6$ to $C_{10}$ aryl, which may be substituted by one to three groups selected from CN, OH, $NO_2$, $C_1$ to $C_{30}$ aralkyl and $C_1$ to $C_{30}$ alkaryl.

Of the above formulae, compounds in which the Z group or groups represent CH (carbocyclic aromatic compounds) are especially preferred, as are compounds in which the various substituents comprise only carbon, hydrogen and oxygen. Compounds in which the specified substituents include aryl groups are less preferred, in view of the possibility of competing reactions in which acylation occurs at plural locations.

Preferably, in the above structures:
$R^1$ is selected from hydrogen; $C_1$ to $C_{20}$ straight chain or branched alkyl or $C_3$ to $C_8$ cycloalkyl wherein said alkyl or cycloalkyl group may be substituted with 1–3 substituents independently selected from: $C_6$ to $C_{10}$ aryl, $C_8$–$C_{20}$ aralkyl, $C_8$–$C_{20}$ alkaryl, $C_3$ to $C_8$ cycloalkyl, hydroxyl, F, $CF_3$, =O or $OR^3$ wherein $R^3$ is selected from H, $C_1$ to $C_{20}$ alkyl and $C_6$ to $C_{10}$ aryl; or $C_6$ to $C_{10}$ aryl; and $R^2$ represents $C_1$ to $C_{20}$ straight chain or branched alkenyl or $C_5$ to $C_8$ cycloalkenyl wherein said alkenyl or cycloalkenyl group may be substituted with 1–3 substituents independently selected from $C_1$ to $C_{20}$ alkyl, $C_6$ to $C_{10}$ aryl, $C_8$–$C_{20}$ aralkyl, $C_8$–$C_{20}$alkaryl, hydroxyl, F, $CF_3$, =O or $OR^3$ wherein $R^3$ is selected from H, $C_1$ to $C_{20}$ alkyl and $C_6$ to $C_{10}$ aryl; or $C_6$ to $C_{10}$ aryl.

Also preferred are compounds of the above structures wherein:
$R^1$ is selected from hydrogen; $C_1$ to $C_{10}$ straight chain or branched alkyl; and
$R^2$ represents $C_1$ to $C_{20}$ straight chain or branched alkenyl or $C_5$ to $C_8$ cycloalkenyl wherein said alkenyl or cycloalkenyl group may be substituted with 1–3 substituents independently selected from $C_1$ to $C_{20}$ alkyl or $C_6$ to $C_{10}$ aryl.

Especially preferred are those compounds wherein:
$R^1$ is selected from hydrogen; $C_1$ to $C_{10}$ straight chain or branched alkyl; and
$R^2$ represents $C_1$ to $C_{20}$ straight chain or branched alkenyl or $C_5$ to $C_8$ cycloalkenyl wherein said alkenyl or cycloalkenyl group may be substituted with $C_1$ to $C_{10}$ alkyl or phenyl.

DEFINITIONS

Unless indicated otherwise, the terms used herein have the meanings as indicated below:

"Alkyl" (including alkyl portions of alkyoxy, alkaryl, aralkyl, alkylamino, dialkylamino) represents straight and branched carbon chains containing from 1 to 40 carbon atoms, preferably 1 to 40 carbon atoms, and more preferably 4 to 12 carbon atoms.

"Cycloalkyl" represents saturated carbocyclic rings branched or unbranched containing from 3 to 20 carbon atoms, preferably 3 to 8 carbon atoms. Such cycloalkyl groups include cyclopentyl and cyclohexyl.

"Heterocycloalkyl" represents a saturated, branched or unbranched carbocyclic ring containing from 3 to 12 carbon atoms, preferably from 4 to 6 carbon atoms, wherein the carbocyclic ring is interrupted by 1 to 3 heteroatom moieties selected from —O—, or —N($C_1$ to $C_6$ alkyl), or NH. Such heterocycloalkyl groups include 2- or 3-tetrahydrofuranyl, 2-, 3- or 4-piperidinyl, 2-, 3- or 4-piperizinyl, morpholinyl, 2- or 3-pyrrolidinyl and 2- or 4-dioxanyl.

"Alkenyl" represents straight and branched carbon chains having at least one carbon to carbon double bond and containing from 2 to 40 carbon atoms, preferably 2 to 20 carbon atoms and more preferably from 2 to 12 carbon atoms. Thus, the term "alkenyl" as used herein includes dienes (including conjugated dienes) trienes and tetraenes.

"Cycloalkenyl" represents saturated carbocyclic rings branched or unbranched containing from 3 to 20 carbon atoms, preferably 3 to 8 carbon atoms, wherein the ring contains at least one C=C bond. Cyclohexenyl and cyclopentenyl are particularly preferred cycloalkenyl groups.

"Alkynyl" represents straight and branched carbon chains having at least one carbon to carbon triple bond and containing from 2 to 20 carbon atoms, preferably 2 to 20 carbon atoms and more preferably from 2 to 12 carbon atoms.

"Aryl" including aryl moieties in e.g. aralkyl represents a carbocyclic group containing from 6 to 15 carbon atoms (preferably from 6 to 10 carbon atoms) and having at least one aromatic ring, with all available substitutable carbon atoms of the carbocyclic group being intended as possible points of attachment. Preferred aryl groups include phenyl and naphthyl. Unless otherwise indicated, the term "aryl" includes such carbocyclic groups being optionally substituted with, 1 to 3 of the following substituents: $C_1$ to $C_6$ alkyl, OH, O($C_1$ to $C_6$ alkyl), phenoxy, $CF_3$, ($C_1$ to $C_6$ alkyl)amino, di($C_1$ to $C_6$ alkyl)amino, —COO($C_1$ to $C_6$ alkyl) or $NO_2$.

"Heteroaryl" represents cyclic groups having at least one heteroatom selected from —O— or —N—, said heteroatom interrupting a carbocyclic ring structure and having a sufficient number of delocalised pi electrons to provide aromatic character, with the aromatic heterocyclic groups preferably containing from 2 to 14 carbon atoms. Suitable heteroaryl groups include pyridine, indole, imidazole, pyridazine, pyrazine, oxazole, triazole, pyrazole, and purines and pyrimidines.

The temperature at which the acylation reaction is carried out is preferably between 15° C. and 250° C., most preferably between 80 and 180° C.

The invention may also be defined as comprising a process in which a zeolites acts as a catalyst or catalyst precursors carried out in an ionic liquid medium, which in a preferred embodiment utilises an acylating agent.

Where an acylating reagent is reacted with an aromatic compound (e.g. benzene) the result of the process will be the production of an aromatic ketone. A specific example is where a benzoylating agent is reacted with an aromatic ether such as anisole to produce para-methoxybenzophenone. The ratio between the number of moles of aromatic ether and the number of moles of acylation agent is preferably between 0.2 and 25, most preferably between 0.5 and 15. The quantity of zeolite catalyst preferably is from 0.05% to 30% by weight of the aromatic ether, most preferably between 1.0% and 20%.

The term "ionic liquid" refers to a liquid that is capable of being produced by melting a solid, and when so produced, consists solely of ions. Ionic liquids may be derived from organic salts, especially salts of heterocyclic nitrogen-containing compounds, and such ionic liquids are particularly preferred for use in the processes of the present invention, and are referred to herein as "organic ionic liquids".

An ionic liquid may be formed from a homogeneous substance comprising one species of cation and one species of anion, or can be composed of more than one species of cation and/or anion. Thus, an ionic liquid may be composed of more than one species of cation and one species of anion. An ionic liquid may further be composed of one species of cation, and one or more species of anion.

Thus, in summary, the term "ionic liquid" as used herein may refer to a homogeneous composition consisting of a single salt (one cationic species and one anionic species) or it may refer to a heterogeneous composition containing more than one species of cation and/or more than one species of anion.

The term "ionic liquid" includes compounds having both high melting temperature and compounds having low melting points, e.g. at or below room temperature (i.e. 15–30° C.). The latter are often referred to as "room temperature ionic liquids" and are usually derived from organic salts having pyridinium and imidazolium-based cations.

A feature of ionic liquids is that they have particularly low (essentially zero) vapour pressures. Many organic ionic liquids have low melting points (e.g. less than 100° C., particularly less than 100° C., and around room temperature, e.g. 15–30° C. Some have melting points well below 0° C.

Ionic liquids may thus be regarded as consisting of two components, which are a positively charged cation and a negatively charged anion. Generally, any compound that meets the criteria of being a salt (consisting of an anion and cation) and which is fluid at or near the reaction temperature, or exists in a fluid state during any stage of the reaction can be defined as an ionic liquid especially suitable for use in the process of the present invention.

Especially suitable ionic liquids for use in the present invention include salts of alkylated or polyalkylated heteroaryl compounds, such as salts of alkylated pyridine, pyridazine, pyrimidine, pyrazine, imidazole, pyrazole, oxazole and triazole. Thus, examples of suitable ionic liquids include those having the following formula:

wherein
R$^a$ is a C$_1$ to C$_{40}$, (preferably C$_1$ to C$_{20}$ and more preferably C$_4$ to C$_{12}$) straight chain or branched alkyl group or a C$_3$ to C$_8$ cycloalkyl group, wherein said alkyl or cycloalkyl group which may be substituted by one to three groups selected from: C$_1$ to C$_6$ alkoxy, C$_6$ to C$_{10}$ aryl, CN, OH, NO$_2$, C$_1$ to C$_{30}$ aralkyl and C$_1$ to C$_{30}$ alkaryl;

R$^b$, R$^c$, R$^d$, R$^e$ and R$^f$ can be the same or different and are each independently selected from H or any of the R$^a$ groups as defined above; and A represents an anion having a charge n−; wherein n may be 1–3. Preferably, in the above compounds, n is 1.

Preferably, R$^a$ is an unsubstituted alkyl or cycloalkyl group as defined above. R$^b$, R$^c$, R$^d$, R$^e$ and R$^f$ are preferably hydrogen.

In preferred ionic liquids for use in the processes of the present invention, the cation is preferably 1,3-dialkylimidazolium. Other cations for this process include other substituted pyridinium or alkyl- or poly-alkylpyridinium, alkyl imidazolium, imidazole, alkyl or poly-alkylimidazolium, alkyl or polyalkylpyrazolium, ammonium, alkyl or poly-alkyl ammonium, alkyl or poly-alkyl phosphonium cations.

Particularly preferred ionic liquids are imidazolium, pyridinium or pyrazolium salts. Thus, ionic liquids useful for the process of the present invention include those based on imidazolium cations having the formula:

wherein
each R$^a$ may be the same or different and each is independently selected from C$_1$ to C$_{40}$ straight chain or branched alkyl which may be substituted by one to three groups selected from: C$_1$ to C$_6$ alkoxy, C$_6$ to C$_{10}$ aryl, CN, OH, NO$_2$, C$_1$ to C$_{30}$ aralkyl and C$_1$ to C$_{30}$ alkaryl;

A represents one or more species of anion having charge n−; and n represents 1–3.

Also suitable for the processes of the present invention are ionic liquids based on pyridinium cations having the formula:

wherein
R$^a$ is selected from C$_1$ to C$_{40}$ straight chain or branched alkyl which may be substituted by one to three groups selected from: C$_1$ to C$_6$ alkoxy, C$_6$ to C$_{10}$ aryl, CN, OH, NO$_2$, C$_1$ to C$_{30}$ aralkyl and C$_1$ to C$_{30}$ alkaryl;

A represents one or more species of anion having charge n−; and n represents 1–3.

Preferably, in the above ionic liquids, R$^a$ is independently selected from C$_1$ to C$_{40}$, preferably C$_1$ to C$_{20}$, and even more preferably, C$_4$ to C$_{12}$, straight chain or branched alkyl.

Preferred ionic liquids include those of the above formulae wherein A represents a single species of anion having charge n−; anions having a charge of 1 are especially preferred.

Examples of anions "A" anions include sulfur-containing anions such as sulfate, sulphite and alkyl sulfate, nitrogen-containing anions, such as nitrate, nitrite and anions containing an amide moiety, halide, including fluoride, chloride, bromide and iodide, hydrogensulfate, oxoanions of metals, (including selenium, tellurium, phosphorus, arsenic, antimony, bismuth based anions) and boron halide anions, such as tetrafluoroborate, [BF$_4$].

Ionic liquids particularly useful in the present processes include those wherein A represents an anion selected from boron or phosphorus fluorides, NO$_3$, SO$_4$, HSO$_4$, HCO$_3$, [(CF$_3$SO$_2$)$_2$N], [AsF$_6$], alkylsulfonates, mono- or difluorinated alkyl sulfonates including perfluorinated alkylsulfonates, carboxylic acid anions, fluorinated carboxylic acid anions and metal halides.

Especially preferred are ionic liquids having the above formulae wherein A represents an anion selected from [PF$_6$], [BF$_4$], [OSO$_2$CF$_3$], [OSO$_2$(CF$_2$)$_3$CF$_3$], [OCO$_2$CF$_3$], [OCO$_2$(CF$_2$)$_3$CF$_3$], [OCO$_2$CH$_3$], nitrate, sulfate, hydrogen sulfate, hydrogen carbonate, acetate, trifluoroacetate, lactate, [(CF$_3$SO$_2$)$_2$N], [B(alkyl)$_4$] wherein each alkyl can be the same or different and can be any straight chain or branched C$_1$ to C$_{10}$ alkyl (preferably C$_1$ to C$_6$ alkyl) group, [SbF$_6$]$^-$ and [AsF$_6$].

Even more preferred are ionic liquids of the above formulae wherein A represents an anion selected from [PF$_6$], [BF$_4$], [OSO$_2$CF$_3$], [OSO$_2$(CF$_2$)$_3$CF$_3$], [OCO$_2$CF$_3$], [OCO$_2$(CF$_2$)$_3$CF$_3$], [OCO$_2$CH$_3$], [(CF$_3$SO$_2$)$_2$N], [B(alkyl)$_4$] wherein each alkyl can be the same or different and can be any straight chain or branched C$_1$ to C$_{10}$ alkyl (preferably C$_1$ to C$_6$ alkyl) group, [SbF$_6$]$^-$ and [AsF$_6$].

The anions [PF$_6$] (hexafluorophosphate), [BF$_4$] (tetrafluoroborate) and [(CF$_3$SO$_2$)$_2$N] {bis[(trifluoromethyl)sulfonyl] amide or bistriflimide) are particularly preferred, especially for the imidazolium- and pyridinium-cation-based ionic liquids.

More than one ionic liquid or any combination of ionic liquids may be used in the present invention.

Specific examples of ionic liquids include:
1-butyl-3-methylimidazolium hexafluorophosphate ([bmim][PF$_6$]), 1-ethyl-3-methylimidazolium bis((trifluoromethyl)sulphonyl)amide ([emim][NTf$_2$]),
1-butyl-3-methylimidazolium bis((trifluoromethyl)sulphonyl)amide ([bmim][NTf$_2$]),
1-ethyl-2,3-dimethylimidazolium bis((trifluoromethyl) sulphonyl)amide ([C$_2$dmim][NTf$_2$]),
1-butyl-3-methylimidazolium tetrafluoroborate ([bmim][BF$_4$])

The use of ionic liquids in accordance with the invention is applicable to reactions catalysed by a wide range of zeolites. Zeolites are crystalline aluminosilicates with fully cross-linked open framework structures made up of corner-sharing SiO$_4$ and AlO$_4$ tetrahedra. A representative empirical formula of a zeolite is $$M_{2/n}O \cdot xAlO_3 \cdot ySiO_2 \cdot zH2O$$

where M represents the exchangeable cation of valence n. M is generally a Group I or II ion, although other metal, non-metal and organic cations may also balance the negative charge created by the presence of Al in the structure. The symbols x, y and z are generally in the range 1 to 10, more preferably 1 to 5. The framework may contain cages and channels of discrete size, which are normally occupied by water.

In addition to Si$^{4+}$ and Al$^{3+}$, other elements can also be present in the zeolitic framework. They need not be isoelectronic with Si$^{4+}$ or Al$^{3+}$, but must be able to occupy framework sites. Aluminosilicate zeolites display a net negative framework charge, but other molecular sieve frameworks may be electrically neutral.

Thus, the term "zeolite" as used herein refers to any naturally occurring or synthetic crystalline substance with a structure characterized by a framework of linked tetrahedral, each consisting of four O atoms surrounding a cation. This framework contains open cavities in the form of channels and cages. These are usually occupied by H$_2$O molecules and extra-framework cations that are commonly exchangeable. The channels are large enough to allow the passage of guest species. In the hydrated phases, dehydration occurs at temperatures mostly below about 400° C. and is largely reversible.

Recent advances in structural zeolite chemistry have been mainly in the areas of highly siliceous zeolites, aluminophosphates and related materials. Zeolite chemistry is thus no longer confined to aluminosilicates. Taking into account isomorphous substitution as well as the possible presence of hydroxyl bridges and ligands, the following general formula for a four-connected network of a zeolite-like molecular sieve has been proposed.

The framework of a molecular sieve is based on an extensive three-dimensional network in which the polyhedral sites, usually tetrahedral, are linked by oxygen atoms. The crystalline framework contains cages and channels of discrete size and 3–30 Å in diameter. The primary building unit of a molecular sieve is the individual tetrahedral unit. The topology of all known molecular sieve framework types can be described in terms of a finite number of specific combinations of units.

Molecular sieves have found widespread industrial applications as highly selective adsorbents, ion exchangers and, most importantly, catalysts of exceptionally high activity and selectivity in a wide range of reactions.

The most important application of molecular sieves is as catalysts. Zeolites combine high acidity with shape selectivity, high surface area and high thermal stability and have been used to catalyse a variety of hydrocarbon reactions, such as cracking, hydrocracking, alkylation and isomerisation. The reactivity and selectivity of zeolites as catalysts are determined by the active sites brought about by a charge imbalance between the silicon and aluminium atoms in the framework. Each framework aluminium atom induces a potential active acid site. In addition, purely siliceous and AlPO$_4$ molecular sieves have been BrØnsted acid sites whose weak acidity seems to be caused by the presence of terminal —OH bonds on the external surface of the crystal.

Typical zeolites have aluminosilicate frameworks with loosely bonded alkali or alkali-earth cations, or both. Molecules of H$_2$O occupy extra-framework positions.

The Si:Al ratio, or, more generally, occupancy of tetrahedral sites by Si, Al, P, Be, Zn, and possibly other elements, varies widely in many zeolites.

Typical zeolites contain alkali metal (Na,K) and/or alkaline earth metal (e.g. Ca) ions which are capable of being exchanged for hydrogen or other cations, including organic cations and metal cations. Thus, for example catalytically active metals such as noble metals (Pt, Pd, Ir) or Group VIII metals (Fe, Ni etc) may be incorporated in the zeolite structure by ion exchange zeolites having a very high Si:Al ratio such as the so-called ZSM-5 zeolite have found widespread use as catalysts for hydrocarbon conversion.

The zeolite may be used alone or mixed with an inorganic matrix or carrier. The matrix can be selected from relatively inert and stable metal oxides such as aluminium oxides, silicon oxides and/or zirconium oxides. The zeolite preferably comprises more than 5% by weight of the total catalyst composition.

Various different physical forms of catalyst compositions can be employed, e.g. powders, granules, and shaped bodies such as spheres and pellets. These shaped bodies may be obtained by extrusion, moulding, compacting or any other known process. Granules or spherules are generally the most advantages as regards both efficiency and ease of use.

Ionic liquids have not been used previously as components of reaction media for any hitherto known zeolite catalysed processes and in view of the advantages demonstrated herein, provide a valuable means for carrying out reactions where selectivity may be poor and/or there are problems with product separation and recycle of the catalyst/solvent system utilising conventional organic and aqueous solvents. Particularly, this application describes the first application of zeolites together with ionic liquids as catalysts or catalytic mediators for acylation and benzoylation reactions. In ionic liquids, both the solvent and catalyst are easily recyclable and the reactions performed show enhanced rates over either solventless or conventional organic solvent supported reactions.

The invention will now be described in more detail with reference to the accompanying drawings and the following examples, in which an acylating reagent is reacted with an aromatic compound to form an aromatic ketone:

In the examples, the conversion and rate data were obtained from samples analysed by HPLC.

EXAMPLES

Example 1

Figure 1:
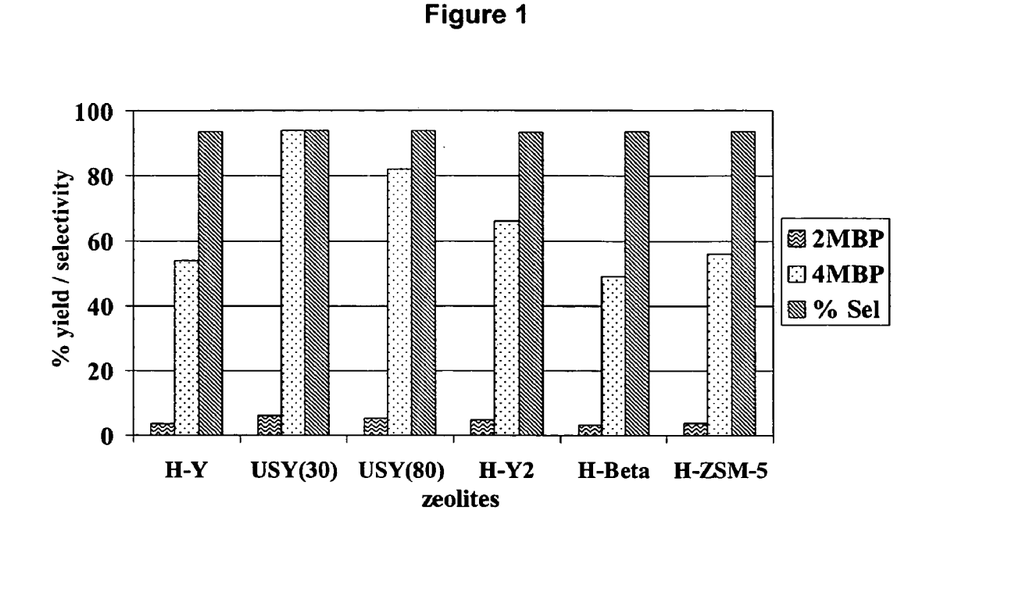
FIG. 1 illustrates the variation in selectivity with respect to ortho-(2MBP) and para-(4MBP) methoxybenzophenone with zeolite type following reaction of benzoic anhydride with anisole in [emim][NTf$_2$] at 80° C. for 1 hour.

Reaction of Benzoic Anhydride with Anisole 0.0046 moles of anisole and 0.005 moles of benzoic anhydride (mole ratio 1:1.1) were mixed with 3 g of 1-ethyl-3-methylimidazolium bis((trifluoromethyl)-sulphonyl)amide, [emim][NTf$_2$], and 0.1 g zeolite and heated to 80° C. Samples were taken after 1 hour and the mixture and analysed by HPLC. FIG. 1 shows the percentage yields of ortho- and para-methoxybenzophenone using a range of zeolites. Each zeolite was activated at 500° C. in dry air for 4 hours prior to use.

Figure 2:
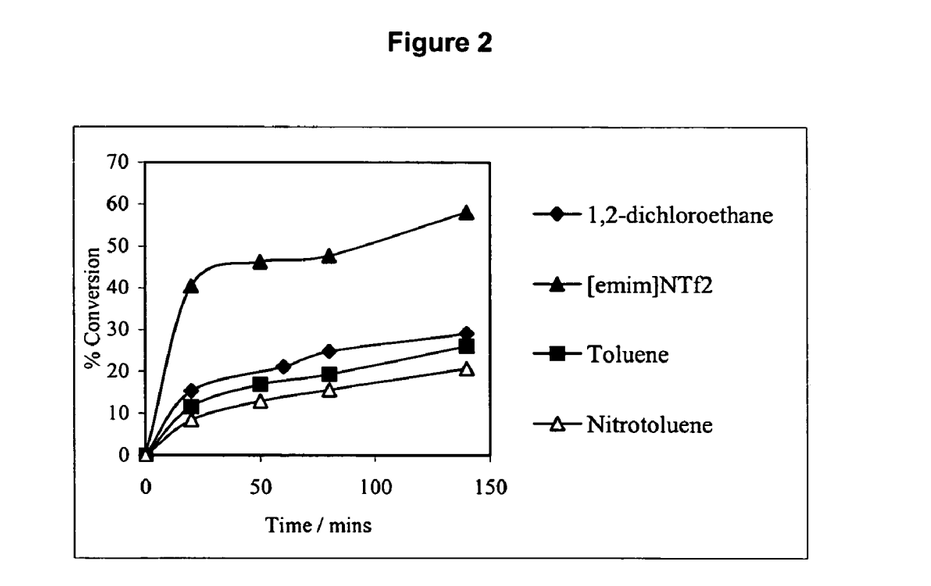
FIG. 2 is a comparison of the reaction rate of USY-30 in [emim][NTf$_2$] and conventional solvents.

FIG. 2 shows the effect of ionic liquid in comparison with conventional organic solvents for the benzoylation of anisole using USY(30) zeolite. It is clear that the ionic liquid is not only capable of performing this reaction but also shows rate enhancement over solvents such as toluene, nitrotoluene, 1,2 dichloroethane and solventless systems. In each case 0.0046 moles of anisole and 0.005 moles of benzoic anhydride (mole ratio 1:1.1) were mixed with 2 g of solvent and 0.1 g USY(30) zeolite and heated to 80° C. The zeolite was activated at 500° C. in dry air for 4 hours prior to use. Little variation in the conversion or selectivity was found on changing from [emim]$^+$ to [bmim]$^+$ to [C$_2$dmim]$^+$ cations. Addition of chloride in the form of [bmim]Cl was found to be detrimental.

Removal of the product from the ionic liquid may be performed by solvent extraction using mesitylene or cumene, for example, or by steam stripping. The latter resulted in anisole extraction at 120° C., benzoic acid at 160° C. and methoxybenzophenone at 250° C. The organic compounds were easily separated from the water by decantation, in the case of anisole, and filtration for both benzoic acid and methoxybenzophenone. HPLC and $^1$H-NMR analysis showed the product to be methoxybenzophenone 99.5% purity containing 94% para- and 6% ortho-product. Analysis of the ionic liquid after extraction showed it to be intact with no significant reactants or products remaining. The ionic liquid was recycled with no loss in activity.

Table 1 shows the recycle of H-beta zeolite in [emim][NTf$_2$] using mesitylene extraction. Although there is some deactivation or loss of activity, the zeolites remain highly active on recycle without the need to reactivate the catalyst at temperature. In each case 0.0046 moles of anisole and 0.005 moles of benzoic anhydride (mole ratio 1:1.1) were mixed with 3 g of solvent and 0.2 g H-beta zeolite and heated to 80° C. The zeolite was activated at 500° C. in dry air for 4 hours prior to use for the first reaction only. After 2 hours, the reaction mixture was extracted with 3×5 cm$^3$ mesitylene, which removed 97% of the reactants and products. Fresh reactants were added and the experimental procedure repeated.

TABLE 1

Variation in product distribution and conversion on recycle following reaction of benzoic anhydride with anisole in [emim][NTf$_2$] at 80° C. for 2 hours using 0.3 g H-beta zeolite.

|  | % Conversion | % Selectivity (para-product) |
|---|---|---|
| First reaction | 80 | 94 |
| First recycle | 65 | 94 |
| Second recycle | 50 | 94 |

Table 2 summarizes the solubility of the zeolites used in a range of ionic liquids. 0.1 g of zeolite was heated to 100° C. in 3 g of ionic liquid for 24 hours. The ionic liquid was centrifuged to remove the zeolite and the liquid decanted and analysed for aluminium using ICP-AES. Significant dissolution of the zeolite was found in [PF$_6$]$^-$ and [BF$_4$]$^-$ containing ionic liquids but little dissolution was observed in the case of [NTf$_2$]$^-$ ionic liquids.

TABLE 2

Variation in zeolite dissolution with ionic liquid following contact of 0.1 g catalyst at 100° C. for 24 hours with 3 g ionic liquid.

|  | Al Concentration/ppm |
|---|---|
| [bmim][NTf$_2$] | 7 |
| [bmim][BF$_4$] | 22 |
| [bmim][PF$_6$] | 275 |

Figure 3:
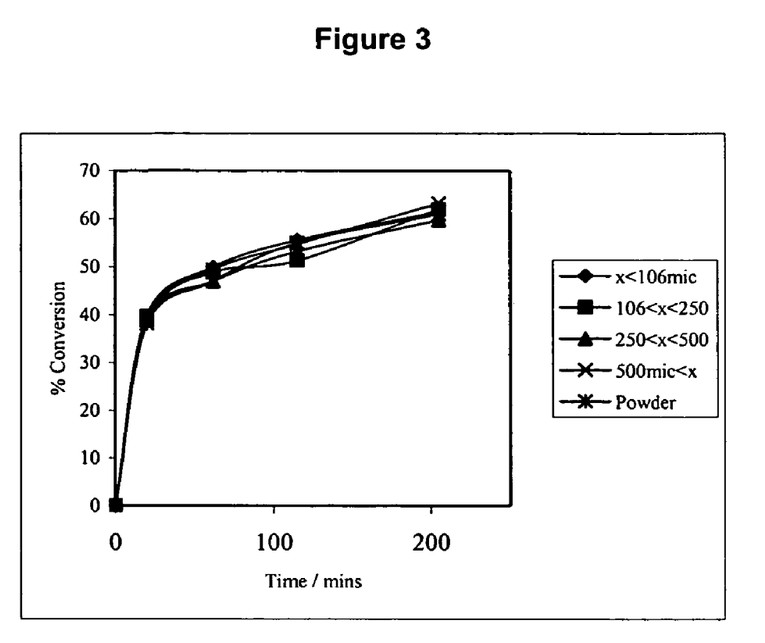
FIG. 3 is a comparison of the reaction rate of different particle sizes (x in microns) of USY-30 in [emim][NTf$_2$].

FIG. 3 shows the effect of zeolite particle size on the rate of reaction. The zeolites were pelletised and sieved to a variety of sizes and activated at 500° C. in dry air for 4 hours prior to use. 0.0046 moles of anisole and 0.005 moles of benzoic anhydride (mole ratio 1:1.1) were mixed with 3 g of 1-ethyl-3-methylimidazolium bis((trifluoromethyl)sulphonyl)amide, [emim][NTf$_2$], and 0.1 g zeolite and heated to 80° C. Samples were taken and the mixture analysed by HPLC. Little change in the rate is observed for all the particle sizes measured.

Example 2

Reaction of Benzoic Anhydride with Anisole Using a CSTR 0.53 moles of anisole, 0.46 moles of benzoic anhydride and 60 g [emim][NTf$_2$] were reacted over 2.2 g USY(30) pelletised into 100 μm particles after being activated at 500° C. in dry air for 4 hours. The zeolite was contained within a wire mesh basket suspended in the reaction mixture and stirred axially at 240 r.p.m. After 30 mins, the reaction was switched from batch to continuous mode operating with an inlet and outlet flow of 0.5 cm$^3$ min$^{-1}$. The inlet flow was made up of ionic liquid and reactants at the same concentration as the initial reaction mixture. The reaction was continued for 4 hours with only a small loss in activity of the zeolite. The deactivation observed was reversible and on recycle and reactivation of the catalyst, the activity was fully restored. Partial activity could also be restored by washing the zeolite with reaction mixture containing no product, which indicates at least some of the deactivation was associated with strong product adsorption.

Example 3

Reaction of Benzoic Anhydride with Anisole Using a PFR

Figure 4:
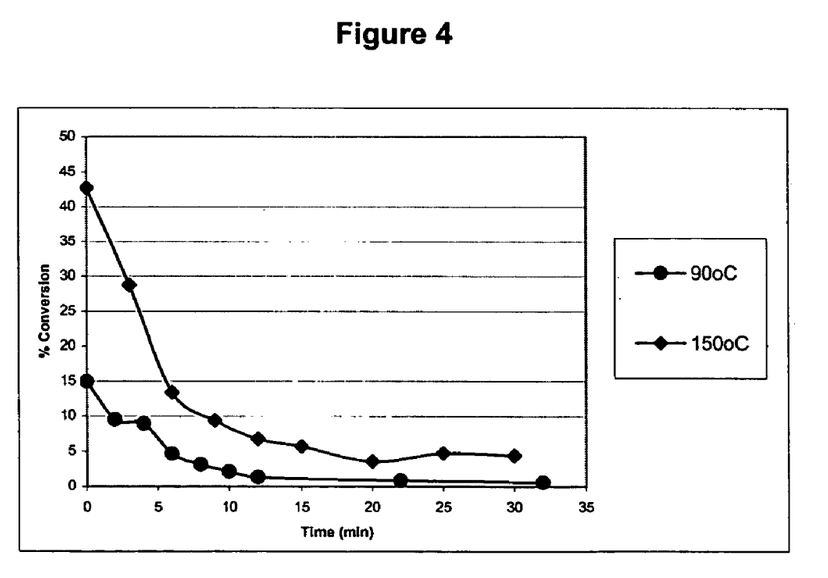
FIG. 4 shows the effect of temperature on conversion in continuous flow using USY-30 catalyst in [emim][NTf$_2$].
Figure 5:
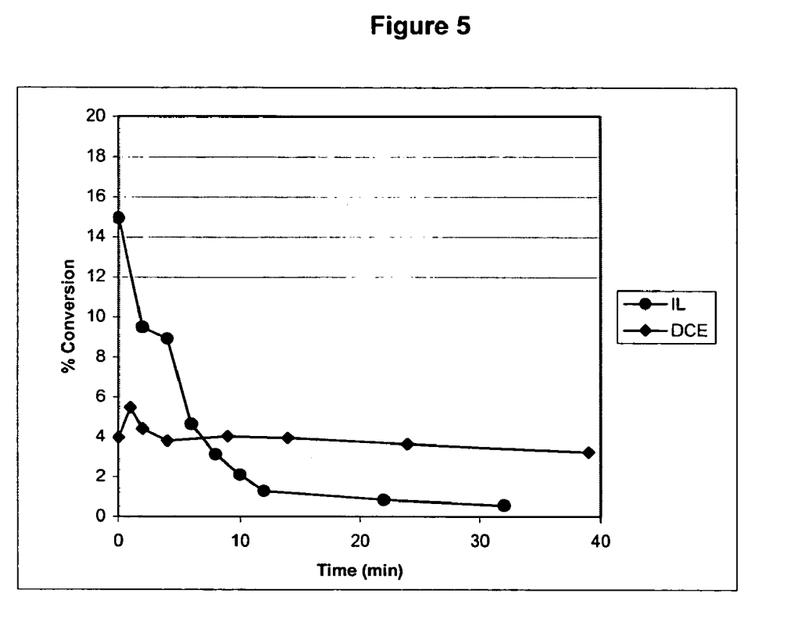
FIG. 5: is a comparison of [emim][NTf$_2$] with DCE when using USY-30 in a PFR.
Figure 6:
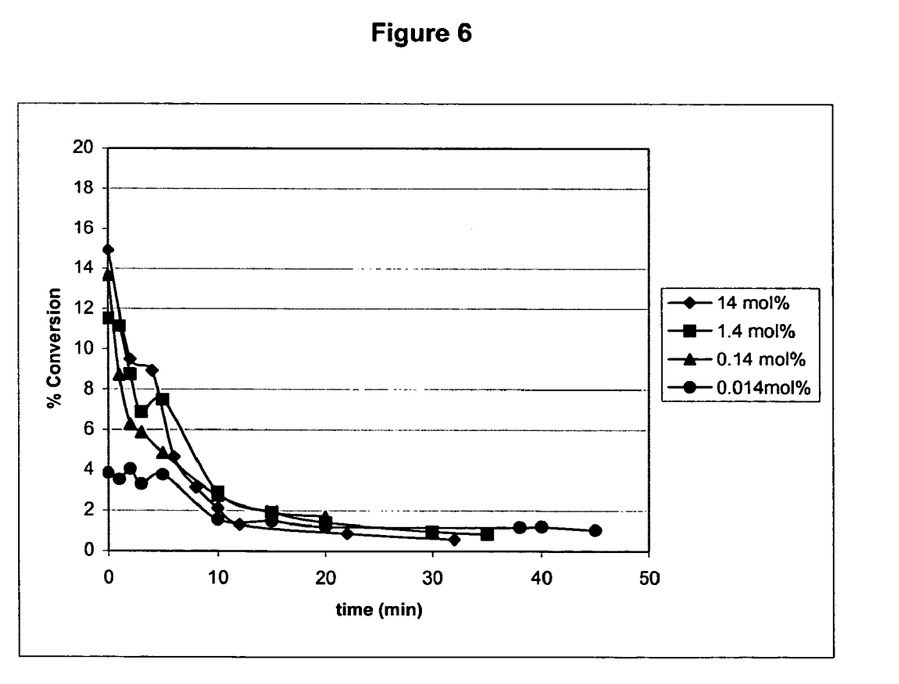
FIG. 6 illustrates the effect of decreasing ionic liquid concentration

A number of reactions were performed in a plug flow reactor using 0.5 g of USY-30 zeolite at an operating temperature of 90° C. (or 150° C. where stated) and a volumetric flow rate of 156 ml hr$^{-1}$. The anisole:benzoic anhydride:ionic liquid ratio ([emim][NTf$_2$]) was 1:2:0.5 respectively. The residence time within the catalyst bed was 10 min. FIG. 4 shows the effect of temperature on the conversion in the PFR reactor indicating a rapid deactivation profile in both cases. This profile is expected if a portion of the zeolite surface acts as an ion exchange medium yielding the acid (i.e. HNTf$_2$) as the actual catalyst, which then washes through the column. This acid is normally internally recycled in the batch cases and partially diluted within the CSTR reaction. FIG. 5 shows a comparison of [emim][NTf$_2$] to 1,2 dichloroethane. Again a rapid deactivation is observed in the ionic liquid case compared to the more stable 1,2 dichloroethane, although the initial activity in the Ionic liquid is much higher. FIG. 6 shows the time on stream conversions for varying mole ratios of [emim][NTf$_2$], this supports the ion exchange effect mentioned above. All samples were analysed by HPLC.

Example 4

Reaction of Acetic Anhydride with Anisole 0.13 moles of anisole and 0.14 moles of acetic anhydride (mole ratio 1:1.1) were mixed with 3.8 g of and 1 g zeolite and heated to 120° C. Samples were taken after 5 mins and 1 hour and analysed by HPLC. Table 3 shows the percentage yields of 2- and 4-methoxyacetophenone using H-ZSM5 and H-beta zeolites. Each zeolite was activated at 500° C. in dry air for 4 hours prior to use.

TABLE 3

Variation in conversion following reaction of acetic anhydride with anisole in [bmim][NTf$_2$] and solvent less at 130° C. using H-ZSM5 and H-beta zeolite.

|  | % conversion | |
| --- | --- | --- |
| Catalyst | 5 mins | 1 hour |
| H-ZSM5 | 33 | 33 |
| H-Beta | 32 | 40 |
| H-ZSM5 (no solvent) | 20 | 20 |
| H-Beta (no solvent) | 18 | 22 |

(In all cases the selectivity to the para-product was 94%)

Example 5

Reaction of Acetic Anhydride with Toluene

Reactions where carried out at 160° C. and 40 bar in a Baskerville autoclave. Samples were taken after 17 hours and analysed by HPLC.

TABLE 4

Showing the effect of different zeolite catalysts on the acylation of toluene

| Zeolite | Arene/anydride ratio | wt % Toluene conversion | wt % Methylbenzophenone |
| --- | --- | --- | --- |
| Beta | 1:1* | 68.2 | 63.3 |
|  | 1:3 | 94.7 | 93.4 |
| ZSM-5 [Si/Al = 45] | 1:1 | 60.6 | 56.5 |
| USY-30 | 1:1 | 43.6 | 37.3 |
|  | 1:3 | 39.6 | 52.2 |
| Mordenite | 3:1 | 31.8 | 31.8 |
|  | 1:3 | 100 | 92.4 |

*4 hrs in Carius tube @ 160° C.

TABLE 5

Showing the effect of the Toluene/Benzoic anydride ratio on the acylation of toluene

| Toluene/Benzoic anhydride ratio | wt % Toluene conversion | wt % Methylbenzophenone |
| --- | --- | --- |
| 10:1 | 18.5 | 12.1 |
| 3:1 | 38.9 | 30.6 |
| 1:1* | 68.2 | 63.3 |
| 1:3 | 94.7 | 93.4 |

Conditions: Autoclave pressure - 40 Bar, 160° C., 17 hrs, using zeolite beta
*4 hrs in Carius tube @ 160° C.

The ionic liquid solvent was further compared with a traditional solvent, 1,2 dichloroethane and table 6 shows that under identical conditions, using different arene/anhydride ratios, the ionic liquid results in higher toluene conversion.

TABLE 6

The effect of solvent on the acylation of benzene

| Toluene/Benzoic anhydride ratio | Solvent | % Toluene conversion | wt % Methylbenzophenone |
| --- | --- | --- | --- |
| 1:1 | [emim]Tfi | 68.2 | 63.3 |
| 1:3 | [emim]Tfi | 94.7 | 93.4 |
| 1:1 | DCE | 12.1 | 5.6 |
| 1:3 | DCE | 32.6 | 41.3 |

Conditions: Autoclave pressure - 40 Bar, 160° C., 17 hrs, using zeolite beta

The invention claimed is:

1. A method for catalyzing an electrophilic substitution reaction between two or more reactants, said method comprising the steps of contacting:
   1) a zeolite;
   2 a reaction medium comprising an ionic liquid; and
   3) at least two reactants;
   such that the zeolite acts as a catalyst and/or catalyst precursor and electrophilic substitution reaction products are formed.
2. The method according to claim 1 wherein the electrophilic substitution reaction is an alkylation, isomerisation or hydrocracking reaction.
3. The method according to claim 1 wherein the electrophilic substitution reaction is a Friedel-Crafts electrophilic aromatic substitution reaction.

4. The method as claimed in claim 1 wherein the electrophilic substitution reaction is an acylation reaction.

5. The method as claimed in claim 1 wherein the electrophilic substitution reaction is an benzoylation reaction.

6. The method as claimed in claim 1 wherein the ionic liquid is [bmin] [$PF_6$], [emin] [$NTf_2$], [bmin] [$NTf_2$], [$C_2$dmin] [$NTf_2$] or [bmin] [$BF_4$].

7. The method as claimed in claim 1 wherein the zeolite is in hydrogen form prior to the electrophilic substitution reaction.

8. The method as claimed in claim 1 wherein the zeolite is heat activated.

9. The method of claim 1 wherein the zeolite catalyzes the reaction by forming an active catalyst species comprising a reaction product of the zeolite and the ionic liquid wherein the cationic component of the ionic liquid exchanges for protons on metal cations of the zeolite in hydrogen form.

10. The method as claimed in claim 1 wherein the process results in the selective formation of para-methoxybenzophenone.

11. A process comprising the steps of:
1) providing a zeolite;
2) providing a reaction medium comprising an ionic liquid;
3) providing at least two reactants capable of interreacting to form elctrophilic substitution products; and
4) contacting the zeolite, the ionic liquid reaction medium and the at least two reactants such that the at least two reactants undergo an electrophilic substitution reaction in which the zeolite acts as a catalyst and/or catalyst precursor.

12. A process as claimed in claim 11 in which the at least two reactants comprise an acylating agent.

13. A process according to claim 12 wherein the acylating agent has the formula:

and wherein each $R^1$ and $R^2$, which may be the same or different, represents a substituted or unsubstituted aliphatic, aromatic or heterocyclic group containing from 1 to 40, preferably 1 to 25 and most preferably 1 to 10 carbon atoms, and X represents a leaving group.

14. A process as claimed in claim 12 wherein the at least two reactants comprise an aromatic ketone, and said acylating reagent is reacted with an aromatic compound to form an aromatic ketone.

15. A process according to claim 14 wherein the aromatic compound is benzene.

16. A process claimed in claim 11 wherein the ionic liquid is [bmin] [$PF_6$], [emin] [$NTf_2$], [bmin] [$NTf_2$], [$C_2$dmin] [$NTf_2$] or [bmin] [$BF_4$].

17. A process as claimed in claim 11 wherein the at least two reactants comprise a benzoylating agent and anisole and the reaction produces para-methoxybenzophenone.

18. A process as claimed in claim 11 wherein the reaction product is removed from the ionic liquid by solvent extraction or steam stripping.

19. A process as claimed in claim 11 wherein the ionic liquid is recyclable.

20. A process as claimed in claim 11 wherein the zeolite catalyzes the reaction by forming an active catalyst species comprising a reaction product of the zeolite and the ionic liquid wherein the cationic component of the ionic liquid exchanges for protons on metal cations of the zeolite in hydrogen form.

21. A process according to claim 11 wherein the ionic liquid is an imidazolium, pyridinium, pyridazinium, pyrazinium, oxazolium, triazolium or pyrazolium salt.

22. A process according to claim 21 wherein the ionic liquids is a salt of an alkylated or polyalkylated compound of pyridine, pyridazine, pyrimidine, pyrazine, imidazole, pyrazole, oxazole or triazole.

23. A process according to claim 20 wherein the ionic liquid has the formula:

wherein $R^a$ is a $C_1$ to $C_{40}$ straight chain or branched alkyl or $C_3$ to $C_8$ cycloalkyl group, wherein said alkyl or cycloalkyl group which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl; $R^b$, $R^c$, $R^d$, $R^e$ and $R^f$ can be the same or different and are each independently selected from H or any of the $R^a$ groups as defined above; and

A represents an anion having a charge n-; wherein n may be 1–3.

24. A process according to claim 23 wherein $R^a$ represents $C_4$ to $C_{12}$ straight chain or branched alkyl.

25. A process according to claim 23 wherein $R^b$, $R^c$, $R^d$, $R^e$ and $R^f$ are hydrogen.

26. A process according to claim 23 wherein n is 1.

27. A process according to claim 20 wherein the ionic liquid has the formula:

wherein
each $R^a$ may be the same or different and each is independently selected from $C_1$ to $C_{40}$ straight chain or branched alkyl which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;

A represents one or more species of anion having valency n; and n represents 1–3.

28. A process according to claim 20 wherein the ionic liquid has the formula:

wherein
$R^a$ is selected from $C_1$ to $C_{40}$ straight chain or branched alkyl which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl;

A represents one or more species of anion having valency n; and n represents 1–3.

29. A process according to claim 23 wherein A represents a single species of anion having valency n.

30. A process according to claim 23 wherein n is 1.

31. A process according to claim 23 wherein A represents an anion selected from boron or phosphorus fluorides, $NO_3$, $SO_4$, $HSO_4$, $HCO_3$, $[(CF_3SO_2)_2N]$, $[AsF_6]$, alkylsulfonates, mono- or difluorinated alkyl sulfonates including perfluorinated alkylsulfonates, carboxylic acid anions, fluorinated carboxylic acid anions and metal halides.

32. A process according to claim 30 wherein A represents an anion selected from [PF6], $[BF_4]$, $[OSO_2CF_3]$, $[OSO_2(CF_2)_3CF_3]$, $[OCO_2CF_3]$, $[OCO_2(CF_2)_3CF_3]$, [OCO2CH3], nitrate, sulfate, hydrogen sulfate, hydrogen carbonate, acetate, trifluoroacetate, lactate, $[(CF_3SO_2)_2N]$, $[B(alkyl)_4]$ wherein each alkyl can be the same or different and can be any straight chain or branched $C_1$ to $C_{10}$ alkyl group, $[SbF_6]^-$ and $[AsF_6]$.

33. A process according to claim 30 wherein A represents an anion selected from $[PF_6]$, $[BF_4]$, $[OSO_2CF_3]$, $[OSO_2(CF_2)_3CF_3]$, $[OCO_2CF_3]$, $[OCO_2(CF_2)_3CF_3]$, $[OCO_2CH_3]$, $[(CF_3SO_2)_2N]$, $[B(alkyl)_4]$ wherein each alkyl can be the same or different and can be any straight chain or branched $C_1$ to $C_{10}$ alkyl group, $[SbF_6]^-$ and $[AsF_6]$.

34. A process according to claim 30 wherein A represents an anion selected from $[PF_6]$, $[BF_4]$ and $[(CF_3SO_2)_2N]$.

35. The method according to claim 1 wherein the ionic liquid has the formula:

wherein
$R^a$ is a $C_1$ to $C_{40}$ straight chain or branched alkyl or $C_3$ to $C_8$ cycloalkyl group, wherein said alkyl or cycloalkyl group which may be substituted by one to three groups selected from: $C_1$ to $C_6$ alkoxy, $C_6$ to $C_{10}$ aryl, CN, OH, $NO_2$, $C_1$ to $C_{30}$ aralkyl and $C_1$ to $C_{30}$ alkaryl; $R^b$, $R^c$, $R^d$, $R^e$ and $R^f$ can be the same or different and are each independently selected from H or any of the $R^a$ groups as defined above; and A represents an anion having a charge n–; wherein n may be 1–3.

* * * * *